United States Patent
Choi et al.

(10) Patent No.: US 12,158,984 B1
(45) Date of Patent: Dec. 3, 2024

(54) ACTIVITY CARE ZONE SYSTEM HAVING MULTI-FACETED IMAGE STRUCTURE AND MOTION SENSING FUNCTION

(71) Applicant: HUMAN IT SOLUTION CO., LTD., Mokpo-si (KR)

(72) Inventors: Bongdu Choi, Mokpo-si (KR); Hosung Park, Changwon-si (KR)

(73) Assignee: HUMAN IT SOLUTION CO., LTD., Mokpo-si (KR)

( * ) Notice: Subject to any disclaimer, the term of this patent is extended or adjusted under 35 U.S.C. 154(b) by 0 days.

(21) Appl. No.: 18/352,527

(22) Filed: Jul. 14, 2023

(30) Foreign Application Priority Data

May 26, 2023 (KR) .................. 10-2023-0068092

(51) Int. Cl.
| | |
|---|---|
| *G06F 3/01* | (2006.01) |
| *G06F 3/04817* | (2022.01) |
| *G16H 40/63* | (2018.01) |
| *H04N 9/31* | (2006.01) |

(52) U.S. Cl.
CPC .............. *G06F 3/011* (2013.01); *G06F 3/017* (2013.01); *G06F 3/04817* (2013.01); *G16H 40/63* (2018.01); *H04N 9/3147* (2013.01)

(58) Field of Classification Search
CPC ...... G06F 3/011; G06F 3/017; G06F 3/04817; G16H 40/63; H04N 9/3147
See application file for complete search history.

(56) References Cited

U.S. PATENT DOCUMENTS

| | | | | |
|---|---|---|---|---|
| 7,259,747 | B2* | 8/2007 | Bell | H04N 23/56 345/157 |
| 10,074,148 | B2* | 9/2018 | Cashman | E04H 1/1222 |
| 10,412,380 | B1* | 9/2019 | Neira | H04N 13/363 |
| 10,419,716 | B1* | 9/2019 | Tanumihardja | A63F 13/5252 |
| 10,685,478 | B1* | 6/2020 | Laurino | G06F 3/013 |
| 11,740,689 | B1* | 8/2023 | Verplaetse | G03B 17/54 345/156 |
| 2003/0227541 | A1* | 12/2003 | Aoki | H04N 13/279 348/E13.058 |
| 2012/0309532 | A1* | 12/2012 | Ambrus | G06T 11/20 463/36 |
| 2013/0271372 | A1* | 10/2013 | Nasiri | G06F 3/017 345/158 |
| 2014/0204343 | A1* | 7/2014 | Choi | G03B 21/56 353/30 |
| 2014/0226167 | A1* | 8/2014 | Smith | A63F 13/00 353/121 |

(Continued)

*Primary Examiner* — Grant Sitta (57) ABSTRACT

An activity care zone system includes: an image output module including a plurality of image output devices disposed at predetermined positions in an indoor care zone to project images onto multiple surfaces of six surfaces that constitute the indoor care zone except for an open rear side, in which installation positions and irradiation angles of the image output devices are set such that a shadow of a user is not generated within a field of view of the user located at least in a central area of the bottom surface and facing a front surface; a sensing module installed in one area of the indoor care zone to sense a position and a motion of the user; and a control module configured to control such that the image output devices output synchronized images according to a sensing result of the sensing module and a pre-stored scenario.

8 Claims, 8 Drawing Sheets

(56) References Cited

U.S. PATENT DOCUMENTS

| | | | | |
|---|---|---|---|---|
| 2015/0084861 | A1* | 3/2015 | Cheon | G06F 3/04883 |
| | | | | 345/156 |
| 2016/0219338 | A1* | 7/2016 | Wang | H04N 21/4782 |
| 2016/0334697 | A1* | 11/2016 | Kim | G02B 3/08 |
| 2017/0246534 | A1* | 8/2017 | Johnson | A63F 13/98 |
| 2017/0365102 | A1* | 12/2017 | Huston | A63F 13/65 |
| 2018/0256115 | A1* | 9/2018 | Campbell | A61B 5/4023 |
| 2018/0293041 | A1* | 10/2018 | Harviainen | H04N 13/361 |
| 2018/0314322 | A1* | 11/2018 | Tseng | G06T 19/006 |
| 2018/0369702 | A1* | 12/2018 | Hake | A63G 25/00 |
| 2019/0116356 | A1* | 4/2019 | Matoba | H04N 9/3147 |
| 2020/0265638 | A1* | 8/2020 | Koperwas | G02B 27/017 |
| 2020/0404226 | A1* | 12/2020 | Takada | H04N 9/3194 |
| 2021/0011607 | A1* | 1/2021 | Ziman | G06T 19/003 |
| 2021/0069574 | A1* | 3/2021 | O'Dowd | G06F 3/04815 |
| 2021/0110598 | A1* | 4/2021 | Evans | G06F 3/011 |
| 2021/0289178 | A1* | 9/2021 | Ogishita | H04N 9/3194 |
| 2021/0350495 | A1* | 11/2021 | Liu | G06T 7/507 |
| 2024/0069626 | A1* | 2/2024 | Vaish | G06T 19/003 |
| 2024/0078352 | A1* | 3/2024 | Krauthamer | G06F 30/13 |

\* cited by examiner

ACTIVITY CARE ZONE SYSTEM HAVING MULTI-FACETED IMAGE STRUCTURE AND MOTION SENSING FUNCTION

BACKGROUND OF THE INVENTION

1. Field of the Invention

The present invention relates to a technology for enabling use of activity care such as health care by constructing a virtual environment in an indoor room, and more specifically, to a technology for providing a multi-faceted image output structure and an image output form, which can minimize a shadow effect of a user and structurally and naturally output multi-faceted image contents to multiple surfaces.

2. Description of the Related Art

Virtual experience contents collectively refer to contents in which a user wears a head mounted display (HMD) or is located at a space where an image is output so that the user can obtain realistic experience effects through the image output to the device or an indoor space. These experience contents are provided in various forms such as VR, AR, and MR.

Currently, most of the virtual experience content is focused on game contents or media contents. This results from limitations of the contents itself, but also results from limitations of the use, which is caused by occurrence of dizziness due to a difference between a moving speed of contents and a cognitive speed of the user, when using the HMD or the like or when using a sudden motion or a user's motion.

Accordingly, in recent years, there are provided contents that output contents in the indoor space and sense a user's motion to enable use of the contents through interaction with the output contents. Such a form has recently been attempted to be applied to fields such as health care and senior care because it does not cause dizziness and enables relatively simple construction of the system.

Such technologies are typically disclosed in Korean Unexamined Patent Publication Nos. 10-2022-0077079 and 10-2380385. In the related art, disclosed is a system for providing indoor virtual experience contents, which enable experience activities by outputting image contents to a multi-faceted output area (display device) that can be viewed at a wide angle on a location where a user is located to output an immersive image or to output an image to a specific area, and by sensing a user's motion for the image to manipulate or control the contents through interaction with the user's motion.

These technologies are advantageous in that motions and activity care can be performed using the multi-faceted images, but the following problems are raised. Firstly, when the output area has multiple surfaces that constitute a rectangular parallelepiped room in a typical interior, a shadow of the user is generated in the contents according to output of the image, leading to unnatural output and use of the contents such as interfere with use for the contents.

Further, when an input or the like is performed through a motion for the contents, the eyes may be dazzled in a case where the user faces light irradiated from an image output device, leading to a problem in that the contents cannot be naturally used.

SUMMARY OF THE INVENTION

The present invention has been made in an effort to solve the problems in the related art, and specifically, an object of the present invention is to provide a technology for an image output structure, which can minimize output of unnatural contents due to a shadow of a user, in a multi-faceted image output system that uses a rectangular parallelepiped structure in a typical interior as an output area.

In addition, another object of the present invention is to provide an image output control technology which can minimize an effect in which the eyes are dazzled due to irradiated light in order to output image contents by the image output device when the user uses the contents, in the above image output structure.

To achieve the above object, an activity care zone system having a multi-faceted image structure and a motion sensing function according to one embodiment of the present invention, includes: an image output module including a plurality of image output devices disposed at predetermined positions in an indoor care zone to project images onto multiple surfaces of six surfaces that constitute the indoor care zone except for an open rear side, in which installation positions and irradiation angles of the image output devices are set such that a shadow of a user is not generated within a field of view of the user located at least in a central area of the bottom surface and facing a front surface; a sensing module installed in one area of the indoor care zone to sense a position and a motion of the user; and a control module configured to control such that the image output devices output synchronized images according to a sensing result of the sensing module and a pre-stored scenario.

The image output module may include: a first image output device configured to output an image to the front surface; a second image output device including a pair of image output devices that outputs images to left and right surfaces, respectively; a third image output device configured to output an image to a bottom surface which is a floor surface; and a fourth image output device configured to output an image to a top surface which is a ceiling surface, and the first to third image output devices may be installed on the ceiling surface, and the fourth image output device is installed at a rear of an image output area on the bottom surface.

The fourth image output device may be installed at a pillar structure installed at a rear of the image output area on the bottom surface.

The pillar structure may be installed with a kiosk that is used by a user entering the indoor care zone for initial information processing required for using the contents in the indoor care zone.

The first image output device may be installed at a central axis of the top surface to have an irradiation area in a front direction, the pair of second image output devices may be installed with the first image output device interposed therebetween at a position closer to the front surface than an installation area of the first image output device among areas near the central axis of the top surface, the third image output device may be installed at a position closer to the front surface than an installation area of the second image output devices, and irradiation areas of the first to fourth image output devices may not overlap each other.

The third image output device may be buried in an insertion area that is concavely formed on the top surface.

In controlling image output from the image output devices, when a plurality of icons are output for controlling the contents according to a gesture or a position of a user, which is recognized by the sensing module, the control module may control output of the contents such that the icons are output at least to an area located in front of a default position of the user.

The icon may be activated when it is determined that the user's body touches the icon according to a determination result for a motion of a user's body recognized by the sensing module.

The control module may be configured such that, when the images are output from the image output devices, an area where information provided to the user is output is located at least in front of the default position of the user.

The sensing module may include: a kinetic sensor installed in one area of the open rear side in the indoor care zone to sense the motion and body movement of the user; and a LiDAR sensor installed in one area of the front surface in the indoor care zone to sense the position and a posture of the user.

According to the present invention, it is possible to present a structure that can minimize interference of images by hardware such as an image output device in an output area of the image to be recognized by a user, while at the same time, multi-faceted images do not overlap each other, in an activity care zone system which sets the respective surfaces in a typical interior of a hexahedron structure, which are closed except for an open rear side, for example, an area with a door, as areas where images are output based on the field of view at a reference position of the user, and which is provided with contents through interaction with contents that are output by sensing multi-faceted image output for the area and a user's motion.

In particular, the structure can minimize a phenomenon in which a shadow is generated in an image projected to each surface by the user, and can allow the user to recognize only the contents other than the shadow, due to characteristics of installation position and projection direction of the image output device and control for an output form of the image contents by a control unit.

In particular, by minimizing a form in which the user directly faces a light irradiation unit of the image output device by positional characteristics of each image output device and image output control of the control unit, it is possible to maximize natural image output and convenience of use in provision of virtual experience contents through recognition of multi-faceted images and motions by using the typical hexahedron interior.

DETAILED DESCRIPTION OF THE INVENTION

Hereinafter, various embodiments and/or aspects will be disclosed with reference to drawings. In the following description, multiple concrete details will be disclosed in order to help general understanding of one or more aspects for the purpose of description. However, it will be recognized by those skilled in the art that the aspect(s) can be executed without the concrete details. In the following description and accompanying drawings, specific exemplary aspects of one or more aspects will be described in detail. However, the aspects are exemplary, and some equivalents of various aspects may be used, and the descriptions herein are intended to include both the aspects and equivalents thereto.

It is not intended that any "embodiment", "example", "aspect", "illustration", and the like used in the specification is preferable or advantageous over any other "embodiment", "example", "aspect", "illustration", and the like.

Further, the terms "includes" and/or "including" mean that a corresponding feature/or component exists, but it should be appreciated that the terms "include" or "including" mean that presence or addition of one or more other features, components, and/or a group thereof is not excluded.

Further, terms including an ordinal number such as "first" or "second" may be used for the names of various components, not limiting the components. These expressions are used to distinguish one component from another component. For example, a first component may be referred to as a second component and vice versa without departing the scope of the present disclosure. The term "and/or" includes a combination of a plurality of related enumerated items or any of the plurality of related enumerated items.

In addition, unless otherwise defined, all terms used herein, including technical or scientific terms, have the same meaning as commonly understood by one of ordinary skill in the art to which this invention belongs. Terms such as those defined in commonly used dictionaries should be interpreted as having a meaning consistent with the contextual meaning of the related art and should not be interpreted as either ideal or overly formal in meaning unless explicitly defined in the present invention.

Figure 1:
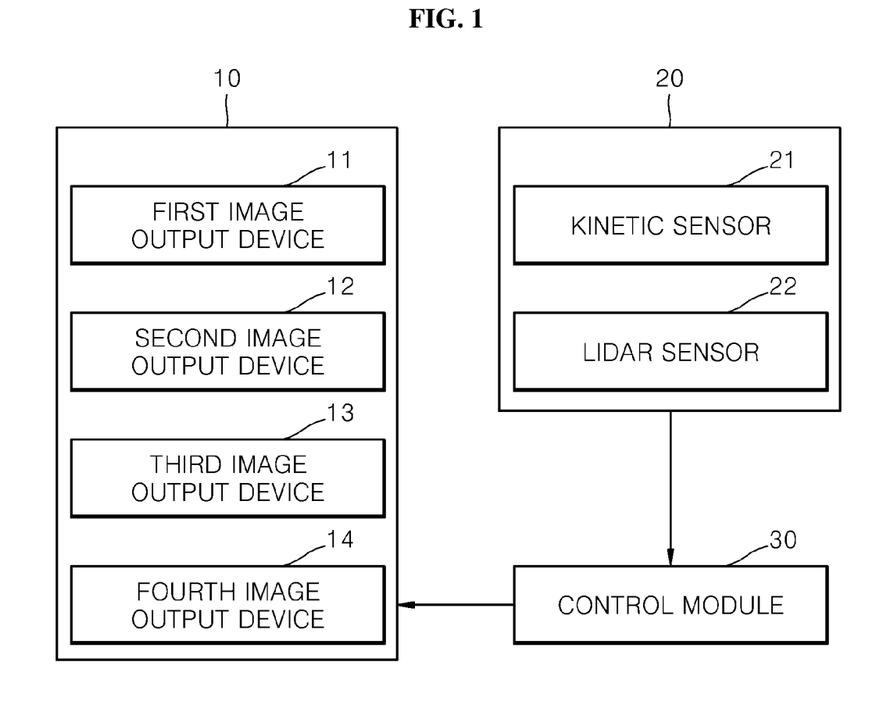
FIG. 1 is a configuration view of an activity care zone system having a multi-faceted image structure and a motion sensing function according to one embodiment of the present invention.
Figure 2:
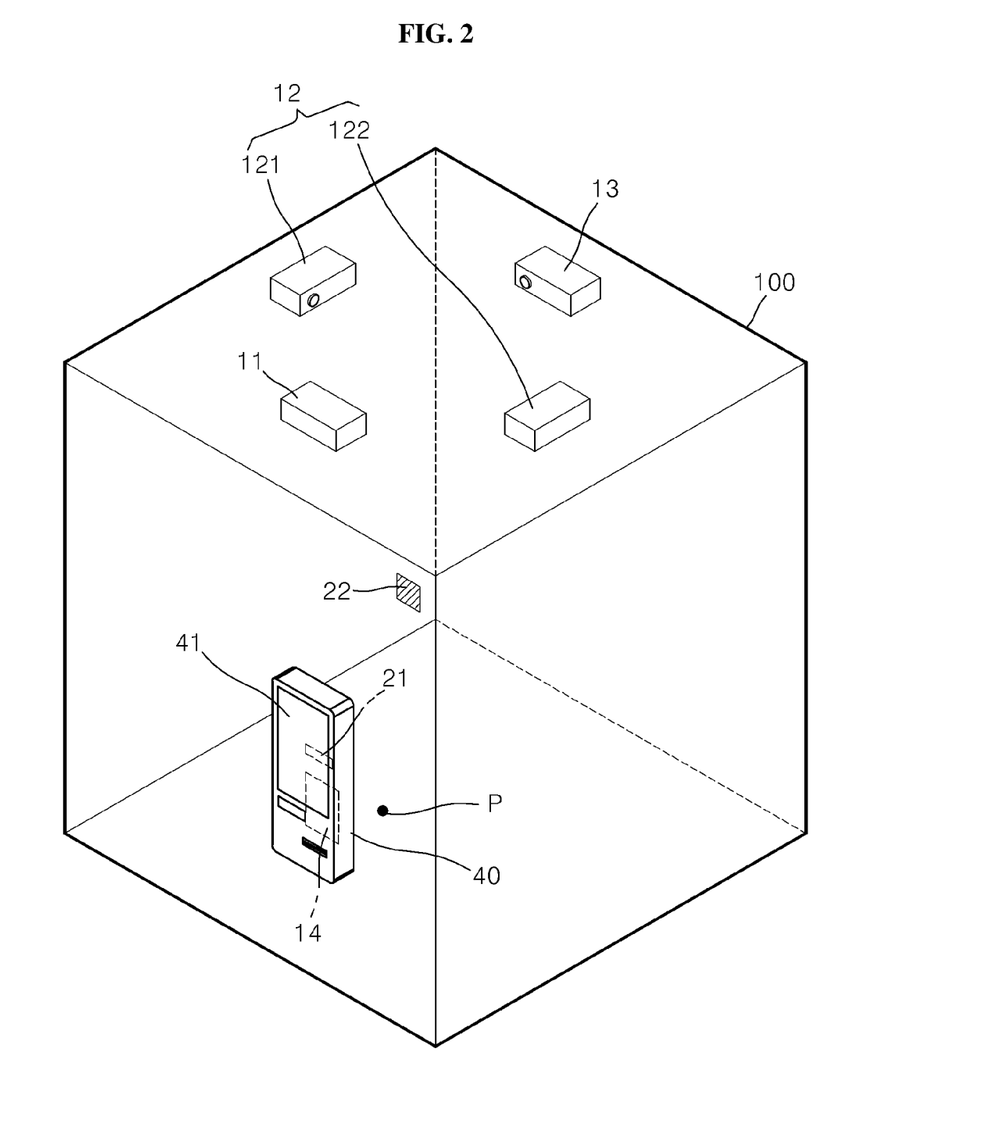
FIG. 2 is a schematic view of an indoor space for explaining an example in which the activity care zone system having a multi-faceted image structure and a motion sensing function is implemented in an interior according to one embodiment of the present invention.
Figure 3:
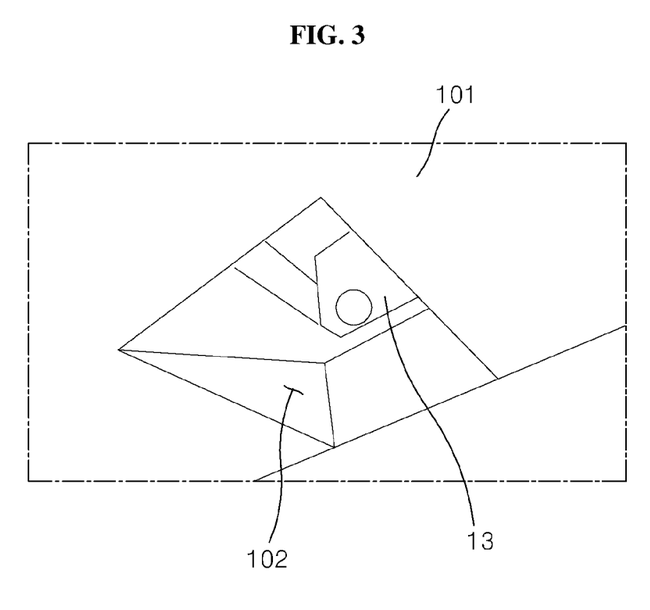
FIG. 3 is a view showing an example of installation form of a third image output device according to implementation of one embodiment of the present invention.
Figure 4:
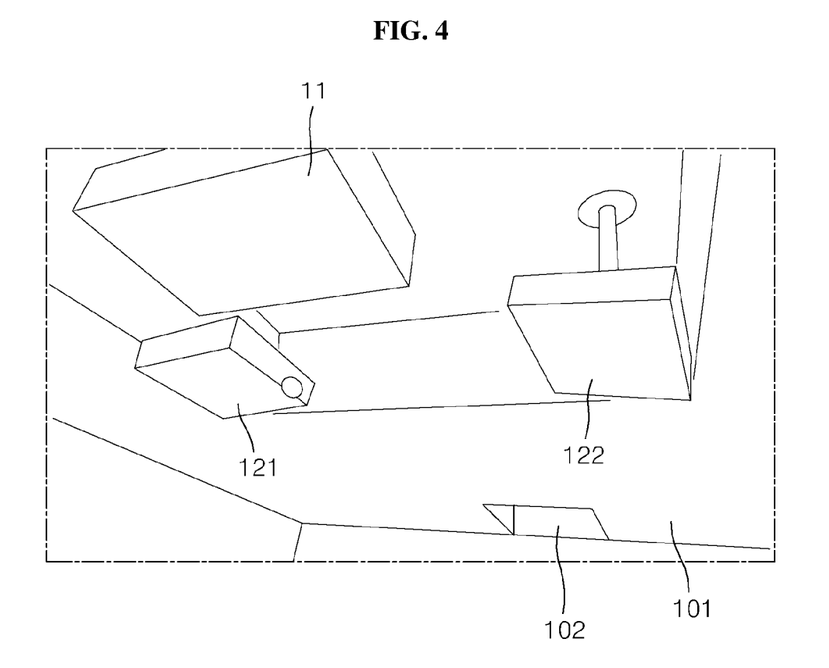
FIG. 4 is a view showing an example of an installation form of first and second image output devices according to implementation of one embodiment of the present invention.
Figure 5:
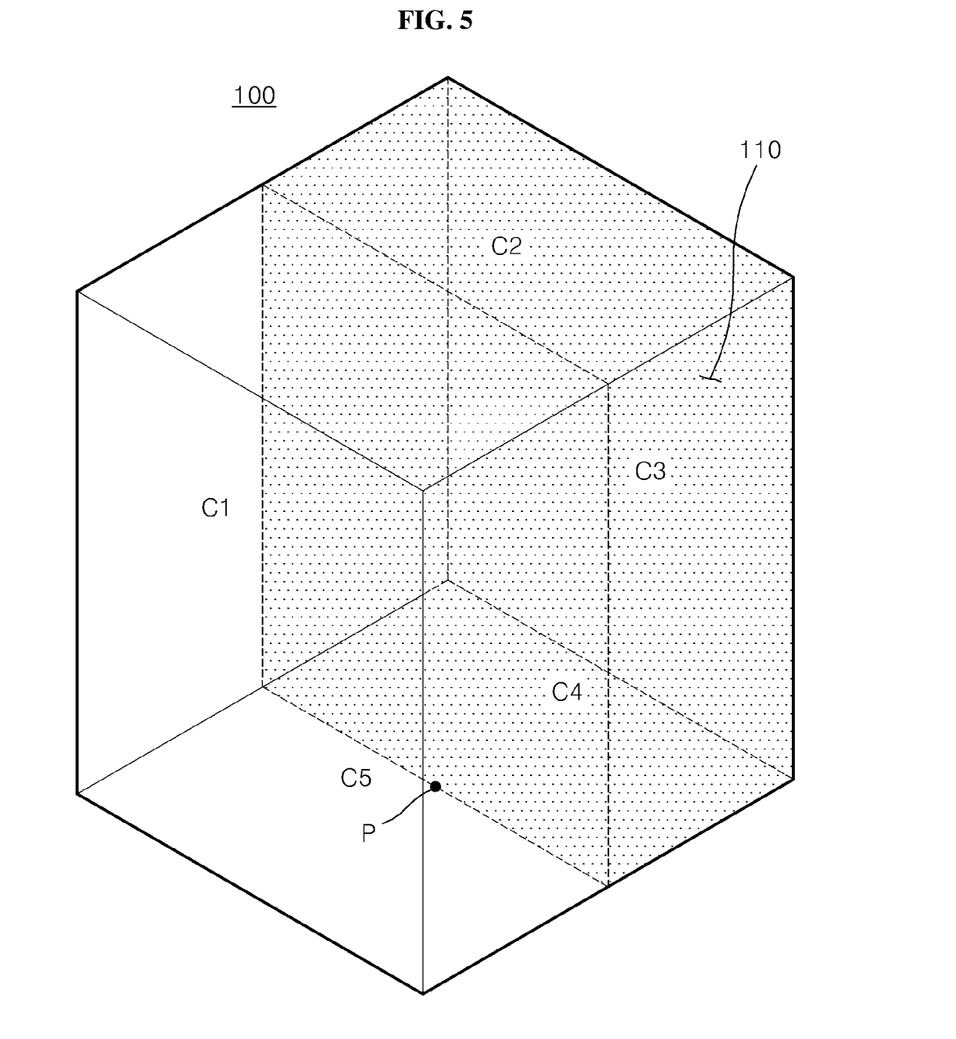
FIGS. 5 to 7 are views for explaining an example of output control of a control unit according to implementation of one embodiment of the present invention.
Figure 6:
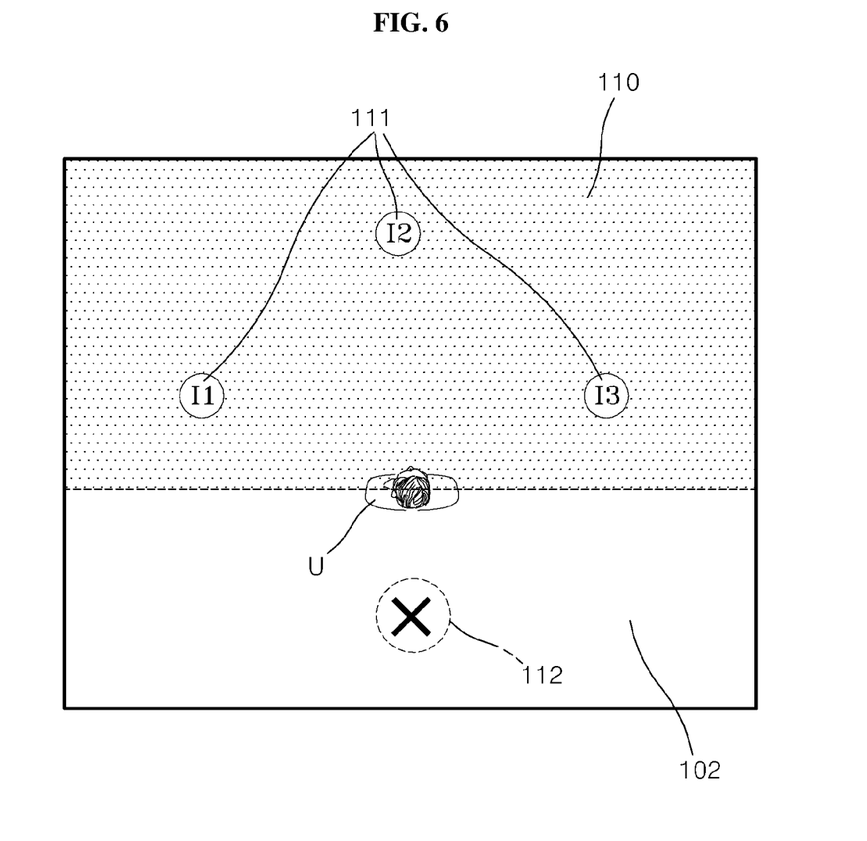
Figure 7:
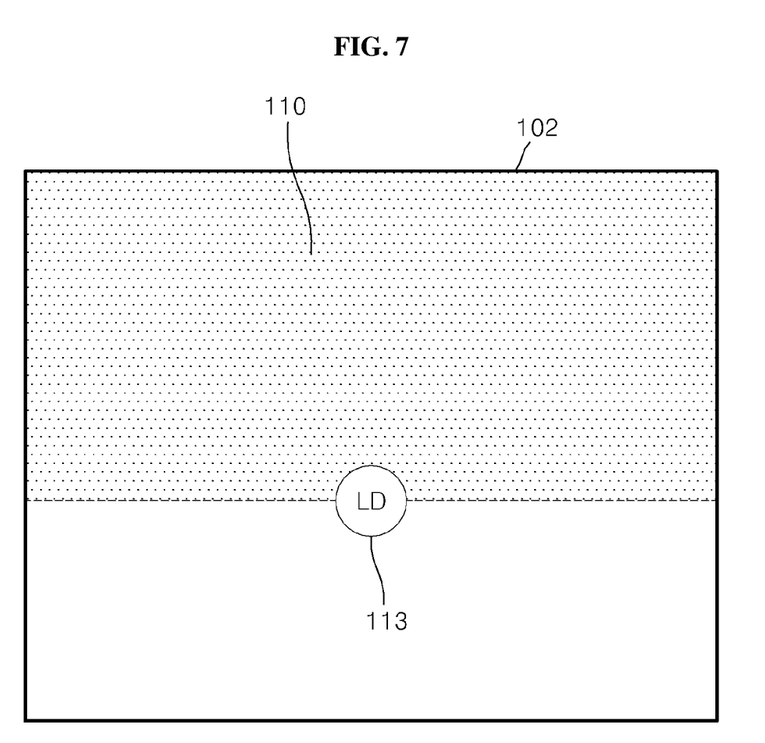

FIG. 1 is a configuration view of an activity care zone system having a multi-faceted image structure and a motion sensing function according to one embodiment of the present invention, FIG. 2 is a schematic view of an indoor space for explaining an example in which the activity care zone system having a multi-faceted image structure and a motion sensing function is implemented in an interior according to one embodiment of the present invention, FIG. 3 is a view showing an example of installation form of a third image output device according to implementation of one embodiment of the present invention, FIG. 4 is a view showing an example of an installation form of first and second image output devices according to implementation of one embodiment of the present invention, and FIGS. 5 to 7 are views for explaining an example of output control of a control unit according to implementation of one embodiment of the present invention. In the following description, the descriptions will be made with reference to a plurality of accompanying drawings in order to describe various embodiments and technical features of the present invention.

Referring to the drawings, an activity care zone system (hereinafter referred to as "system of the present invention") having a multi-faceted image structure and a motion sensing function according to one embodiment of the present invention includes an image output module 10, a sensing module 20, and a control module 30. The system of the present invention may include the control module 30, and in order to transmit/receive and process data according to performing functions of the respective components to be mentioned in the following description, the image output module 10 and the sensing module 20 may include a computing device, which will be described later in the description of FIG. 8, or may be configured as a computing device.

The image output module 10 refers to a configuration of a groupware including a plurality of image output devices disposed at predetermined positions in an indoor care zone to project images onto multiple surfaces of six surfaces that constitute the indoor care zone except for an open rear side, in which installation positions and irradiation angles of the image output devices are set such that a shadow of a user is not generated within a field of view of the user located at least in a central area of the bottom surface and facing a front surface.

According to the present invention, the indoor care zone refers to a space which is provided to function as a screen for generating images by reflecting light irradiated from the image output module 10 as described above, and which is provided for the user who is located in the indoor care zone to confirm the images and manipulate the same or guide the user from the images to perform an activity. The image output in the present invention is visual output data for functioning as content that guides the user to perform a specific behavior or action, and the indoor care zone may function as a screen of the images.

Further, as shown in FIG. 2, the indoor care zone is preferably defined as a space of a hexahedron (preferably, a rectangular parallelepiped or a cubic), which may be defined as a space such as a typical room or the like, without a separate construction of an indoor structure.

The indoor care zone is a door area through which the user enters and exits, and in the present invention, when an opposite side of the indoor care zone is set as a front surface where the user faces at a default position, the indoor care zone is preferably defined such that a rear area of the user, that is, the rear surface is open. The expression "the rear area is open" herein means that an entrance door may be installed as described above or the rear area may be defined while being completely open, and particularly means that the images are not output in the functions of the present invention.

Accordingly, the image output module 10 includes a plurality of image output devices that output the images to the front surface, both side surfaces, the ceiling (top surface), and the floor surface (bottom surface), which are multiple surfaces except for the rear side, that is, the rear surface, that is, the maximum of five surfaces, of six surfaces that constitute the inner care zone as described above.

According to the present invention, each image output device refers to a device which has the same or different image quality and output specifications, and irradiates light corresponding to image data to output an image to each surface of the indoor care zone as light is reflected on each wall surface, ceiling surface, or floor surface in the indoor care zone. For example, a high-resolution beam projector or the like may be configured as the image output device of the present invention.

In this case, the plurality of image output devices are disposed and installed at predetermined installation positions in the indoor care zone. In this case, regarding the installation position of the image output devices, the installation positions and irradiation angles of the image output devices may be set such that a shadow is not generated in an area which is located at least in a central area of the bottom surface, and indicates the front surface.

To this end, referring to at least FIG. 2, the installation position and the irradiation angle of each image output device are preferably set such that the irradiation angle is not set toward the central area of the bottom surface including a reference position P of the user and toward the inside of an area of an image which the user may face when light passes as high as an average height of the user.

According to the present invention, as described above, in order to minimize a phenomenon in which the shadow is generated in the image projected onto each surface by the user who acts on the bottom surface, and recognize only the contents other than the shadow by the user, the installation positions of the plurality of image output devices of the image output module 10 may be set as shown in FIG. 2.

Referring to FIG. 2, first, the image output devices of the image output module include a first image output device 11, second image output devices 12, 121, and 122, a third image output device 13, and a fourth image output device 14.

The first image output device 11 refers to a device that outputs an image toward the front surface, which is recognized when the user faces in a direction of passing through and entering the open rear surface at the position P in the indoor care zone 100. Meanwhile, the second image output device 12 is a pair of image output devices 121 and 122, and is a device that outputs images on both side surfaces based on the front surface, such as a left surface and a right surface. The third image output device 13 is a device that outputs an image to a bottom surface, that is, a floor surface based on the front surface, and the fourth image output device 14 is a device that outputs an image to a top surface, which is a ceiling surface, based on the front surface.

In this case, in order to minimize a shadow phenomenon as described above and minimize a dazzling phenomenon of the user, which is caused by directly irradiating light to the eyes of the user who mainly faces the front surface, the fourth image output device 14 is preferably installed at a rear of the user, specifically, at a rear of the image output area on the bottom surface.

Meanwhile, the other image output devices 11, 12, and 13 are preferably installed on the ceiling surface as shown in FIG. 2 to minimize generation of the shadow described above and minimize interference of images due to optical interference therebetween and dazzling phenomenon.

In this structure, to prevent generation of a shadow, minimize interference of image data due to overlapping of irradiation areas of light irradiated between the image output devices, and prevent dazzling of the user, a specific installation position of the image output device as shown in FIGS. 2 to 4 may be determined.

First, as mentioned in the drawings described above, since the first image output device 11 may be installed at the central axis of the top surface 101 as described above, that is, in the central area, the first image output device 11 may be disposed to have an irradiation area in a front direction. Based on the first image output device 11, a pair of second image output devices 121 and 122 may be installed at a position closer to the front surface than the installation area of the first image output device 11 in the vicinity of the central axis of the top surface 101, that is, in the central area. In this case, for the above-described purpose, the pair of image output devices 121 and 122 may be installed with the first image output device 11 interposed therebetween.

In addition, the pair of image output devices 121 and 122 may be installed as shown in FIG. 4 such that lenses to which light is irradiated are disposed at opposite sides in a direction in which the pair of image output devices 121 and 122 face each other, thereby preventing damage to image contents due to interference between light irradiated from each lens.

Accordingly, the irradiation areas of the first to fourth image output devices 11, 12, 13, and 14 may not overlap each other.

Meanwhile, the third image output device 13 may be installed on the top surface to irradiate light toward the bottom surface, and as shown in FIG. 2, when the third output device 13 may be installed on the top surface, that is, the ceiling surface as it is, the irradiated light is highly likely to be directly irradiated to the user facing the front surface, resulting in inconvenience due to dazzle and unavailability of content recognition.

In order to prevent such a phenomenon, according to one embodiment of the present invention, the third image output device 13 is preferably installed on the ceiling surface, that is, the top surface 101, and is preferably installed in an insertion area 102 that is concavely formed in the top surface 101, as shown in FIGS. 3 and 4. In addition, in this case, the irradiation angle is set such that light is directly irradiated toward the bottom surface through a configuration that does not allow interference by the insertion area 102, thereby minimizing a phenomenon in which the light is directly irradiated to the user's eyes even when the user faces the light.

Meanwhile, as shown in FIG. 2, the fourth image output device 14 is installed at a rear of the default position P of the user to irradiate light toward the ceiling surface, that is, the top surface. In this case, preferably, the installation height of the fourth image output device 14 may be set such that the light irradiation area is not included in an average height of the user, but in this case, the light irradiation area may overlap with the first to third image output devices 11, 12, and 13 described above.

To this end, according to the present invention, the fourth image output device 14 may be installed at the rear of the default position P of the user, and may be installed at a predetermined height (for example, 0.5 m to 1 m) from the bottom surface, so as to have an oblique light irradiation area toward the top surface. Accordingly, it is possible to generate a shadow, but the generation of such a shadow may not give a great inconvenience to the use of the contents, since the user rarely faces the ceiling surface.

Regarding the installation position, in order to fix the installation position and angle of the fourth image output device 14, the fourth image output device 14 may be installed in a pillar structure 40 installed at the rear of the image output area on the bottom surface as shown in FIG. 2.

According to the present invention, the pillar structure 40 is a structure for supporting the fourth image output device 14 as described above, and in this case, a component for performing other functions is mounted on the pillar structure 40 to perform various functions other than the simple support structure, thereby providing convenience to users.

To this end, as shown in FIG. 2, according to the present invention, the pillar structure 40 is not only installed with the fourth image output device 14, but also installed with one component 21 of the sensing module to be described later, and may be installed with a kiosk 41 which is selectively and simultaneously disposed on a surface facing the entrance or an opposite surface thereof and is used by a user entering the indoor care zone 100 for initial information processing required for using the contents in the indoor care zone 100.

Through the component 21 and the kiosk 41, when the user enters the door, the user does not need to input personal information or the like through manipulation of the image output from the image output module 10 from the beginning. According to the present invention, manipulation for the image is performed through body motion recognition by the sensing module 20 to be described later, since a procedure such as input or confirm of the personal information includes complicated manipulation such as selection of characters, numbers, or images, and selection of menus, or the like, it is very inconvenient to perform the manipulation through the body motion recognition. In addition, in order for an administrator to assist the user by performing the manipulation on the contents while the user performs an activity at the default position P or the like, a separate input unit is required.

According to the present invention, the kiosk 41 is installed according to the needs, and is installed for use when the user inputs initial personal information, or the like for performing activities and managing personal activity histories, or when the administrator assists the user in manipulating contents.

Meanwhile, when the user who confirms images output to the multiple surfaces performs manipulation on contents available through the images or performs an activity according to the use of the contents, the sensing module 20 performs a function of recognizing the activity. In this case, since the manipulation of the contents or the performance of the activity is conducted by the user's motion, the sensor module 20 may be understood as a concept of a groupware including one or more sensors installed in one area of the indoor care zone to perform a function of sensing the user's position and motion.

Specifically, the sensing module 20 may include a kinetic sensor 21 and a LiDAR sensor 22. The kinetic sensor 21, which is a large-sized sensor, may block the field of view of the user for image contents when installed on a front surface of the pillar structure 40, so that the kinetic sensor 21 may be installed in one area of the open rear side of the indoor care zone 100, for example, the above-described pillar structure 40 as shown in FIG. 2. The kinetic sensor 21 mainly performs a function of sensing the motion and the body movement of the user according to characteristics thereof.

The LiDAR sensor 22 is a small sensor, and may be installed in one area of the front surface in the indoor care zone 100 to sense a position and a posture of the user.

Through the sensors, when sensing data of each of the sensors 21 and 22 are combined, the position, posture, movement, gesture, or the like of the user may be precisely sensed.

The control module 30 performs a function of controlling such that the image output devices 11, 12, 13, and 14 output synchronized images according to a sensing result of the sensing module 20 and a pre-store scenario.

The control of the image output according to the sensing result of the sensing module 20 means that, when the control module 30 receives a sensing result value from the sensing module 20, the control module 30 generates a control command for the contents based on the position, posture, motion, gesture, or the like of the user, which is recognized according to the sensing result, and outputs an image corresponding to the contents controlled based on the control command. In addition, the control of the synchronized output means that the images output from the respective surfaces are synchronized and output in a time period in which the images need to be output to each other in various cases such as a case in which an image output from each image output device is contents for an activity, a case in which an event for manipulating and controlling the above-described contents occurs, etc.

For example, when the user moves to a specific position, if an event occurs to display a position of the user to an area corresponding to the position or if an icon or the like is positioned in an area of a floor surface corresponding to the position, an area of a side surface or front surface touched by a user's hand or foot, the position is sensed by manipulation of the icon to perform a function corresponding thereto, thereby manipulating the contents.

In addition, the control module 30 may sense the motion of the user or the like to manipulate and control the contents by duplicating the motion of the user or performing a motion paired corresponding to the motion of the user, etc. through a character who is being output from the image in response to the motion of the user, thereby outputting an image corresponding to the manipulation and control of the contents.

In this case, in outputting the image output device described above, there is a highest possibility that a shadow is generated at a rear of the user, and in particular, when the user turns his or her field of view to face backward due to the installation position of the fourth image output device 14 and the light irradiation angle, a dazzling phenomenon may occur.

In order to minimize the unnaturalness of the image output due to such a phenomenon and the inconvenience of the dazzling phenomenon, the control module 30 may limit an output area of specific data or an output area of the entire image data among the image data output while being included in the contents.

For example, referring to FIG. 6, in controlling the image output from the image output devices, when outputting a plurality of icons 111 for controlling the contents according to the gesture or position of the user, which is recognized by the sensing module 20, the control module 30 may control the output the contents to output the icons 111 at least in an area located in front of the default position P of the user.

That is, when the user performs an activity or manipulates the contents, the user needs to move to a specific icon or performs a motion while facing the specific icon, and in this case, the icons are not output to a rear area 112 where the user needs to face backward such that the user face only the front surface.

As described above, the icon 111 may be understood as an icon activated when it is determined that the user's body touches the icon according to a determination result for a motion of the user's body recognized by the sensing module 20. The activation of the icon refers to all visual data for controlling or manipulating a function of the contents available to the user through the image output in the present invention, including, for example, execution/cancellation of specific activity contents, input and cancellation of content execution, etc.

Meanwhile, as shown in FIGS. 5 and 7, the control module 30 may form an area where information provided to the user is output in an area 110 which is located at least in front of the default position P of the user, when the images are output from the image output devices to output corresponding images C1 to C5 to the multiple surfaces.

In this case, when the user starts an activity at the default position P by guiding a reference position 113 as shown in FIG. 7, since the information is confirmed only in the area 110 based on a floor surface 102, the user may perform the activity while facing the front surface or the side surface and manipulating the contents or confirming the information even if the position is located slightly forward, so that when the user faces backward, it is possible to recognize a shadow or minimize a dazzling phenomenon due to the fourth image output device 14.

Figure 8:
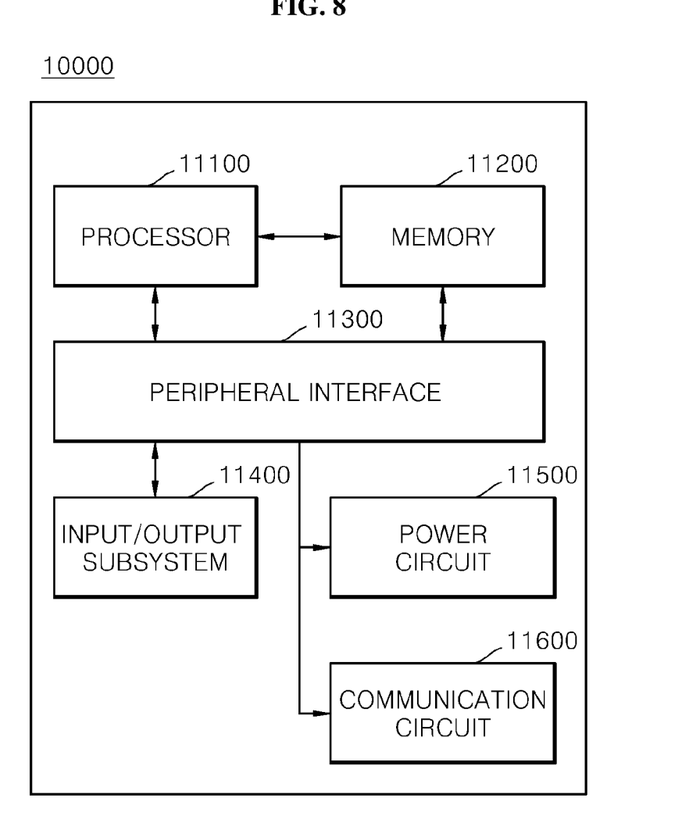
FIG. 8 is a view showing an example of an internal configuration of a computing device according to one embodiment of the present invention.

FIG. 8 shows an example of an internal configuration of a computing device according to one embodiment of the present invention. In the following description, unnecessary descriptions for embodiments redundant with those of FIGS. 1 to 7 will be omitted.

As shown in FIG. 8, a computing device 10000 may at least include at least one processor 11100, a memory 11200, a peripheral interface 11300, an input/output (I/O) subsystem 11400, a power circuit 11500, and a communication circuit 11600. In this case, the computing device 10000 may correspond to a user terminal A connected to a tactile interface device or correspond to the above-described computing device B.

The memory 11200 may include, for example, a high-speed random access memory, a magnetic disk, an SRAM, a DRAM, a ROM, a flash memory, or a non-volatile memory. The memory 11200 may include a software module, an instruction set, or other various data necessary for the operation of the computing device 10000.

In this case, access to the memory 11200 from other components of the processor 11100 or the peripheral interface 11300, may be controlled by the processor 11100.

The peripheral interface 11300 may combine an input and/or output peripheral device of the computing device 10000 to the processor 11100 and the memory 11200. The processor 11100 may execute the software module or the instruction set stored in the memory 11200, thereby performing various functions for the computing device 10000 and processing data.

The input/output subsystem 11400 may combine various input/output peripheral devices to the peripheral interface 11300. For example, the input/output subsystem 11400 may include a controller for combining the peripheral device such as monitor, keyboard, mouse, printer, or a touch screen or sensor, if needed, to the peripheral interface 11300. According to another aspect, the input/output peripheral devices may be combined to the peripheral interface 11300 without passing through the input/output subsystem 11400.

The power circuit 11500 may provide power to all or a portion of the components of the terminal. The power circuit 11500 may include a power management system, one or more power supplies such as a battery or alternating current (AC), a charging system, a power failure detection circuit, a power converter or inverter, a power status indicator, or any other components for power generation, management, and distribution.

The communication circuit 11600 may use at least one external port to enable communication with other computing devices.

Alternatively, as described above, the communication circuit 11600 may include an RF circuit, if needed, to transmit and receive an RF signal, also known as an electromagnetic signal, thereby enabling communication with other computing devices.

The above embodiment of FIG. 8 is merely an example of the computing device 10000, and the computing device 11000 may have a configuration or arrangement in which some components shown in FIG. 8 are omitted, additional components not shown in FIG. 8 are further provided, or at least two components are combined. For example, a computing device for a communication terminal in a mobile environment may further include a touch screen, a sensor or the like, in addition to the components shown in FIG. 8. The communication circuit 11600 may include a circuit for RF communication of various communication schemes (such as WiFi, 3G, LTE, Bluetooth, NFC, and Zigbee). The components that may be included in the computing device 10000 may be implemented by hardware, software, or a combination of both hardware and software which include at least one integrated circuit specialized in a signal processing or an application.

The methods according to the embodiments of the present invention may be implemented in the form of program instructions to be executed through various computing devices so as to be recorded in a computer-readable medium. In particular, a program according to the embodiment of the present invention may be configured as a PC-based program or an application dedicated to a mobile terminal. The application to which the present invention is applied may be installed in a user terminal through a file provided by a file distribution system. For example, a file distribution system may include a file transmission unit (not shown) that transmits the file according to the request of the user terminal.

The above-described device may be implemented by hardware components, software components, and/or a combination of hardware components and software components. For example, the devices and components described in the embodiments may be implemented by using at least one general purpose computer or special purpose computer such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and at least one software application executed on the operating system. In addition, the processing device may access, store, manipulate, process, and create data in response to the execution of the software. For the further understanding, in some cases, one processing device may be used, however, those skilled in the art will be appreciated that the processing device may include a plurality of processing elements and/or a plurality of types of processing elements. For example, the processing device may include a plurality of processors or one processor and one controller. In addition, other processing configurations, such as a parallel processor, are also possible.

The software may include a computer program, a code, an instruction, or a combination of at least one thereof, may configure the processing device to operate as desired, or may instruct the processing device independently or collectively. In order to be interpreted by the processor or to provide instructions or data to the processor, the software and/or data may be permanently or temporarily embodied in any type of machine, component, physical device, virtual equipment, and computer storage medium or device. The software may be distributed over computing devices connected to networks, so as to be stored or executed in a distributed manner. The software and data may be stored in at least one computer-readable recording medium.

The method according to the embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts. Examples of computer-readable recording media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention, or vice versa.

While the embodiments have been described with reference to limited examples and drawings as described above, it will be apparent to one of ordinary skill in the art that various changes and modifications may be made from the above description. Suitable results may be achieved if the described techniques are performed in a different order, and/or if components in a described system, architecture, device, or circuit are combined in a different manner, and/or replaced or supplemented by other components or their equivalents. Therefore, other implementations, other embodiments, and equivalents of the claims are within the scope of the following claims.

What is claimed is:

1. An activity care zone system having a multi-faceted image structure and a motion sensing function, which is implemented by a computing device including one or more processors and one or more memories for storing instructions executable in the processors, the activity care zone system comprising: an image output projector including a plurality of image output devices disposed at predetermined positions in an indoor care zone to project images onto multiple surfaces of six surfaces that constitute the indoor care zone except for an open rear side, in which installation positions and irradiation angles of the image output devices are set such that a shadow of a user is not generated within a field of view of the user located at least in a central area of the bottom surface and facing a front surface;
   a sensor installed in one area of the indoor care zone to sense a position and a motion of the user; and
   a controller configured to control such that the image output devices output synchronized images according to a sensing result of the sensor and a pre-stored scenario, wherein the plurality of image output devices comprises:
   a first image output device, located on a ceiling surface of the indoor care zone, configured to output an image to the front surface;
   a second image output device, located on the ceiling surface of the indoor care zone, which includes a pair of image output devices that output images to left and right surfaces, respectively;
   a third image output device located on the ceiling surface of the indoor care zone and outputting images to a bottom surface of the indoor care zone,
   wherein the third image output device is positioned between a center of the ceiling surface and a sidewall of the indoor care zone the user faces when interacting with the projected images, thus preventing shadows of the user from appearing within a field of view of the user; and wherein the third image output device is fully recessed into the ceiling surface such that the user is not directly exposed to direct light from the third output device; and a fourth image output device, located on the bottom surface of and inside the indoor care zone, configured to output an image to the ceiling surface.

2. The activity care zone system of claim 1, wherein the fourth image output device is installed at a pillar structure installed at a rear of the image output area on the bottom surface.

3. The activity care zone system of claim 2, wherein the pillar structure is installed with a kiosk that is used by a user entering the indoor care zone for initial information processing required for using the contents in the indoor care zone.

4. The activity care zone system of claim 1, wherein the first image output device is installed at a central axis of the ceiling surface to have an irradiation area in a front direction, the pair of second image output devices are installed with the first image output device interposed therebetween at a position closer to the front surface than an installation area of the first image output device among areas near the central axis of the ceiling surface, the third image output device is installed at a position closer to the front surface than an installation area of the second image output devices, and irradiation areas of the first to fourth image output devices do not overlap each other.

5. The activity care zone system of claim 1, wherein in controlling image output from the image output devices, when a plurality of icons are output for controlling the contents according to a gesture or a position of a user, which is recognized by the sensor module, the controller controls output of the contents such that the icons are output at least to an area located in front of a default position of the user.

6. The activity care zone system of claim 5, wherein the icon is activated when it is determined that the user's body touches the icon according to a determination result for a motion of a user's body recognized by the sensor.

7. The activity care zone system of claim 1, wherein the controller is configured such that, when the images are output from the image output devices, an area where information provided to the user is located at least in front of the default position of the user.

8. The activity care zone system of claim 1, wherein the sensor includes:

a kinetic sensor installed in one area of the open rear side in the indoor care zone to sense the motion and body movement of the user; and a LiDAR sensor installed in one area of the front surface in the indoor care zone to sense the position and a posture of the user.

* * * * *